United States Patent
Miller

(10) Patent No.: US 7,151,084 B2
(45) Date of Patent: Dec. 19, 2006

(54) COMPOUND AND METHOD OF TREATING NEUROGENIC CONDITIONS USING NON-STEROIDAL ANTI-INFLAMMATORY DRUG COMPLEXES

(76) Inventor: Landon C. G. Miller, 325 Queens City Ave., Tuscaloosa, AL (US) 35401

( * ) Notice: Subject to any disclaimer, the term of this patent is extended or adjusted under 35 U.S.C. 154(b) by 0 days.

(21) Appl. No.: 11/023,240

(22) Filed: Dec. 27, 2004

(65) Prior Publication Data

US 2006/0142181 A1    Jun. 29, 2006

(51) Int. Cl.
*A61K 38/02*    (2006.01)
(52) U.S. Cl. .......................................... 514/6
(58) Field of Classification Search .................... None
See application file for complete search history.

(56) References Cited

OTHER PUBLICATIONS

Mojumdar, et al., Chem. Papers, 1999, 53(4), 265-271.*
Tamer Fouad, M.D. "New research published this week in The Lancet medical journal suggests that ibuprofen may counteract the antiplatelet activities of aspirin." www.thedoctorslounge.net, Feb. 16, 2003.
S.C. Mojumdar et al. "Preparation and Properties of Magnesium(II) Compounds with Some Bioactive Ligands" Chem. Papers 53(4)265-271 (1999).
Michael Schmidt et al. "Magnesium Bis[D(-)-Mandelate] Dihydrate and Other Alkaline Earth, Alkali, and Zinc Salts of Mandelic Acid" Z. Naturforsch. 53 b, 1098-1102 (1998).

* cited by examiner

*Primary Examiner*—Anish Gupta
*Assistant Examiner*—Satyanarayana R. Gudibande
(74) *Attorney, Agent, or Firm*—Gifford, Krass, Groh, Sprinkle, Anderson & Citkowski, P.C.

(57) ABSTRACT

A complex is provided for the treatment of neurogenic conditions having the formula:

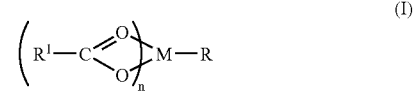

where $R^1$ is

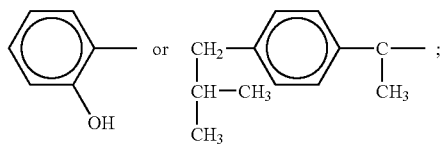

M is a metal ion Ca(II), Mg(II), Cu(II) or Ni(II); n is an integer 1 or 2; R is BBB peptide, transferrin, membrane transporter peptide, TAT peptide, bradykinin, beta-endorphin, bombesin, calcitonin, cholecystokinin, an enkephalin, dynorphin, insulin, gastrin, substance P, neurotensin, glucagon, secretin, somatostatin, motilin, vasopressin, oxytocin, prolactin, thyrotropin, an angiotensin, galanin, neuropeptide Y, thyrotropin-releasing hormone, gonadotropnin-releasing hormone, growth hormone-releasing hormone, luteinizing hormone, vasoactive intestinal peptidegluconate, L-lactate, L-leucine, L-tryptophan, and L-glutamate; and R is coupled to M through a carboxylate moiety. Magnesium(II) represents the preferred metal ion as magnesium is known to have neuroprotective effects. The metal ion is in part chelated by a non-steroidal anti-inflammatory drug that does not inhibit platelet activity and includes salicylate and ibuprofenate. The complex also includes a ligand operative in transport across the blood brain barrier. A process for making an inventive complex includes the stoichiometric addition of ligands containing carboxylate groups to a solution of the metal ion. In instances where the metal ion is magnesium (II), a stoichiometric ratio of 1:1:1 is found between the non-steroidal anti-inflammatory ligand:magnesium(II): transporter ligand.

24 Claims, No Drawings

COMPOUND AND METHOD OF TREATING NEUROGENIC CONDITIONS USING NON-STEROIDAL ANTI-INFLAMMATORY DRUG COMPLEXES

FIELD OF THE INVENTION

The subject invention relates to the treatment of central nervous system injuries and/or conditions and, more particularly, the subject invention relates to the use of non-steroidal anti-inflammatory drug conjugates to traverse the blood brain barrier without impairing platelet clotting for treatment of neurotrauma and neurogenic conditions, and for treatment of diffuse axonal injury associated with human traumatic brain injuries (TBI) and spinal cord injuries (SCI).

BACKGROUND OF THE INVENTION

The predominant mechanism in most cases of traumatic brain injury (TBI) is diffuse axonal injury (Whyte and Rosenthal, 1993). While axonal injury is common in all TBI regardless of severity (Povlishock et al., 1992; Mittl, 1994), a shearing of the axons occurs in human diffuse axonal injury (DAI) leading to progressive changes that ultimately may result in the loss of connections between nerve cells. The slow progression of events in DAI continues for up to several weeks after injury creating a window of opportunity for therapeutic intervention.

There are approximately 500,000 new cases of TBI in the U.S. each year (Frankowski, 1985), and the incidence requiring hospitalization is estimated to be approximately 200–225/100,000 population (Frankowski, 1986; Carus, 1993). Currently, it is estimated that brain injuries account for 12% of all hospital admissions in the United States (Sandel, 1993). When compared to spinal cord injury, which accounts for less than 1% of hospital admissions, it is clear that TBI is a medical care problem which has a significant impact financially within the United States. Approximately 30,000–44,000 people will survive a severe TBI with GCS score <9 (Glasgow Coma Score Scale, Jennett, 1981) in the U.S. each year and more than 70,000 will be significantly disabled from moderate to severe TBI (GCS#10) (Whyte & Rosenthal, 1988). Yet with new medical management techniques, less than 10% will remain in a persistent vegetative state (Whyte, 1993; Rosner, 1992; Rosner, 1990). A GCS score of eight or less generally reflects a state of unconsciousness in which the patient demonstrates no eye opening, does not follow simple commands to move muscles, and has vocalizations which are limited to sounds. Such signs are indicative of severe brain injury (Whyte, 1993; Jennett, 1975; Jennett, 1981).

Approximately 52,000 to 56,000 people die each year from TBI (Kraus et al., 1996), resulting in direct costs approximated at more than $50 billion annually (Max et al., 1991). The costs of severe TBI to the individual and family are extremely high (McMordie, 1988). Acute medical and rehabilitation bills are often around $100,000 with some considerably higher (McMordie, 1988). The Model Systems Database for Traumatic Brain Injury demonstrates there is a correlation between the average Disability Rating Score and the combined acute care and rehabilitation charges (Bullock et al., 1995). Those with a severe TBI (GCS score of 6–8) have average combined charges of $110,842, and those with a very severe TBI (GCS score 3–5) have average combined charges of $154,256 (Lehmkuhl, 1993). About one-half of all TBIs are transportation related (Whyte, 1993; Lehmkuhl, 1993) and these patients have some of the highest combined charges for acute care and rehabilitations (Lehmkuhl, 1993). This may be related to the mechanism of TBI in high speed motor vehicle crashes, specifically the presence of diffuse axonal injury (DAI) being most prevalent in the midbrain and brain stem areas (Whyte, 1993). Clearly, brain injuries of this severity that occur with high speed acceleration-deceleration injuries have the highest costs to society. TBI clearly causes more mortality, morbidity and probably more economic loss than HIV infection in the United States.

Motor vehicle crashes of all types are responsible for approximately 40%–50% of the TBI admissions recorded in the Model TBI Systems Database (Lehmkuhl, 1993). The predominant mechanism of injury is considered to be diffuse axonal injury (DAI). Approximately 30%–40% of the fatal head injuries involve diffuse axonal injury by pathological examination (Bennett et al., 1995; McLellan, 1990). However, based on beta-amyloid precursor protein immunostaining, axonal injury may be present in all cases of fatal head injury (Gentleman et al., 1995). In cases of persistent vegetative states, Kampfl et al. (1998) recently found that all cases had evidence of DAI in magnetic resonance imaging (MRI). Diffuse axonal injury occurs even in the absence of a blow to the head and is more prevalent than previously realized. Even in mild head injury, diffuse axonal injury is present in almost one-third of the cases (Mittl et al., 1994). The defining characteristic of DAI is the morphologic change to the axons which occurs over the course of several days to weeks and the fact that multiple regions of the brain are injured. While a component of DAI is present in blunt or penetrating trauma injury, it is at the periphery of the injury zone and is much less significant than the predominant mechanism of injury. DAI is the major mechanism of injury in high speed acceleration-deceleration injuries associated with motor vehicle crashes. While all four mechanisms of TBI (DAI, blunt trauma, penetrating trauma, axonia) may be involved in such an injury, it is the predominant mechanism of injury under this condition.

For human head injuries resulting from car collisions, the average velocity for the onset of severe injuries is 6.7 m/s (or 24.1 km/hour) as mentioned by Lorenzo et al. (1996). Most studies have been directed to the analysis of impact to the head. The Head Injury Criterion (HIC) is one method that is commonly used to assess the severity of an impact (Chou and Nyquist, 1974). Although it is considered to be the best available head injury indicator, a new finite element model using a dummy head has taken into account the effects of rotational and translational acceleration (Ueno and Melvin, 1995). Using this model, the dominant effect of translational acceleration was on principal stresses and rotational acceleration was on shear stresses.

Current research appears to point of plastic deformation within and of the axons that leads to the predominant cause of injury. The elastic tissues of the brain have plastic properties. Once the level of force is applied to a plastic substance, it is the time period over which it is applied that causes the amount of deformation. If the elastic memory of the substance is exceeded then there will be shearing and tearing. The high speed motor vehicle accident with deceleration lasting more than one to three seconds or several seconds of repetitive shaking can produce enough force for this to happen.

Materials research indicates that there is an amount of force which must be delivered below which plastic deformation of substances does not occur. In fact, the Gadd severity index initially attempted to measure the severity of injury utilizing an acceleration/time curve (Gadd, 1998). This critical amount of force appears to be essential in the development of injury (McLean & Anderson, 1997). This is very different from the contusive model of TBI where the forces are applied over milliseconds.

This indicates that once the amount of force has reached a threshold, it is the length of time the force is applied with the associated plastic deformation that is the predominant factor which causes the intracellular damage to the organelles within the axon. Hence, there is a continuum over which DAI occurs in TBI. After the threshold of necessary force to create plastic deformation is reached, it may be the length of time over which it is applied that determines the amount of DAI. This would explain the findings of Foda et al. (1994) where some DAI was noted in areas adjacent to a contusion injury in rats. Unfortunately, most TBI occurs over several seconds (high speed transportation crashes) where DAI is likely to be the predominant method of injury. This is supported by the fact that many severe TBI patients have minimal changes noted on CT scan following motor vehicle crashes.

Motor vehicle crashes are the predominant cause of DAI. A component of DAI is felt to be present in all motor vehicle crashes where the patient has lost consciousness (Whyte, 1988). For many years, DAI has been known to be associated with a coma of immediate onset after brain injury, but the diagnosis could only be established by autopsy. Indeed, the clinical syndrome of coma without any preceding lucid interval, decerebration, and autonomic dysfunction were often ascribed to primary brainstem injury. However, it is now clear that primary brainstem lesions do not occur in isolation but rather in association with DAI and usually involve the cerebral hemispheres and cerebellum in addition to the brainstem (McLellan, 1990). Evidence of the mechanism of injury can be elicited by pathological studies of patients killed from high speed transportation injuries (Pounder, 1997) as well as pathological studies of "shaken baby syndrome," a distinct subset of DAI (Nelson et al. 1993). A recent case report (Pounder, 1997) indicates that this shaking mechanism of DAI injury also applies to adults. The injury is characterized by specific neuropathological findings. On CT and MRI, this usually involves hemorrhagic punctate lesion of the corpus callosum, pontine-mesencephalic junction adjacent to the superior cerebellar peduncles and diffuse axonal damage in the white matter of the brain, brainstem and cerebellum which begin to atrophy within two weeks after injury (Whyte, 1988; Blumbergs, 1994).

Diffuse axonal injury in humans is characterized by widespread damage to axons in the cerebral hemispheres, the cerebellum and the brain stem and is a consistent feature of TBI (Adams, 1977; Adams, 1989; McLellan, 1990). The histological features of DAI depend on the length of time after injury, but within a day or so after injury there is evidence of damage to axons in the form of axonal bulbs. The initial findings are usually characterized microscopically utilizing neurofibrillar stains and stains for microglia which are abundant in the degenerating white matter. These findings are produced by the shear or flow of cytoplasm from the proximal end of a severed axon. Subsequently, the microscopic features correspond to Wallerian-type axonal degeneration as the axon disintegrates, which is probably due to metabolic disruption from injury and damage to the internal organelles from the lack of membrane integrity. In the first two years there is active myelin degeneration and in patients surviving longer, demyelination is the final stage of the process (McLellan, 1990). The result of the traumatic injury to the axons leads to the disconnection with various target sites, which is assumed to translate into the morbidity seen (Gennarelli, 1982; Povlishock, 1992). The severity of injury based on the histopathological changes has been graded in humans but not in experimental animals (Adams, 1977; Adam, 1989). The Adams classification (Adams, 1977; Adams, 1989) is used in human autopsy material, to classify the degree of DAI as mild, moderate or severe. In this classification, mild (grade 1) is characterized by microscopic changes in the white matter of the cerebral cortex, corpus callosum, and brain stem and occasionally in the cerebellum. Moderate (grade 2) is defined based on focal lesions in the corpus callosum. In severe (grade 3), there are additional focal lesions in the dorsolateral quadrants of the rostral brain stem (commonly in the superior cerebellar peduncle). This scheme has not been used for non-primate models because different regions of the brain are injured in the present models. However, it may be possible to apply this scheme to an appropriate model of DAI in small animals that is currently under development.

When a spinal cord injury or traumatic brain injury occurs, a cascade of damaging events begins which greatly increases the injury to the central nervous system (CNS). One basic factor that has been identified at the center of these events is calcium ($Ca^{++}$) ions.

Up to now, drugs have been used that are only marginally effective in preventing this cascade of events and non-steroidal inflammatory drugs (NSAIDs) have not been useful in animal models for neurotrauma. In part, this may be attributed to the fact that most NSAIDs also inhibit platelet function and consequently may increase bleeding. Furthermore, certain NSAIDs do not cross the blood brain barrier.

Recently there have been a few articles on the use of intrathecal NSAIDs for pain (Pain 1998, Southall et al.; *J. Pharmacol. and Exp. Ther.* 1997; 281:1381–91). Also, U.S. Pat. No. 5,914,129 to Mauskop discloses the use of magnesium containing analgesics for alleviation of pain such as from migraine headaches. Of these drugs aspirin, indomethacin, lysine clonixinate, and ketoprofen have been utilized. PCT/US00/21893 details the use of NSAIDs that are non-inhibitory of platelets especially by intrathecal administration.

While NSAIDs non-inhibitory of platelets are an effective treatment for neuronal injury, intrathecal delivery required because of the inability of such NSAIDs to cross the blood brain barrier has limited the settings in which such a therapy can be provided. Magnesium ions are known to have neuroprotective properties and are especially difficult to deliver across the blood brain barrier alone or as part of an NSAID such as choline magnesium trisalicylate owing to the hydrophilic nature of the ion and the lack of a specific magnesium ion transporter.

Thus, there exists a need for an NSAID conjugate compound capable of traversing the blood brain barrier and thereby be amenable to systemic administration.

SUMMARY OF THE INVENTION

A complex is provided for the treatment of neurogenic conditions having the formula:

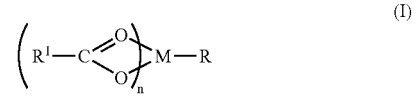
(I)

where $R^1$ is

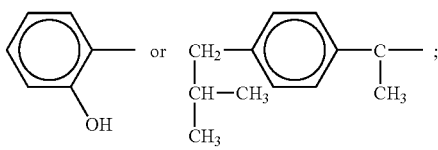

M is a metal ion Ca(II), Mg(II), Cu(II) or Ni(II); n is an integer 1 or 2; R is BBB peptide, transferrin, membrane transporter peptide, TAT peptide, bradykinin, beta-endorphin, bombesin, calcitonin, cholecystokinin, an enkephalin, dynorphin, insulin, gastrin, substance P, neurotensin, glucagon, secretin, somatostatin, motilin, vasopressin, oxytocin, prolactin, thyrotropin, an angiotensin, galanin, neuropeptide Y, thyrotropin-releasing hormone, gonadotropnin-releasing hormone, growth hormone-releasing hormone, luteinizing hormone, vasoactive intestinal peptidegluconate, L-lactate, L-leucine, L-tryptophan, and L-glutamate; and R is coupled to M through a carboxylate moiety. Magnesium(II) represents the preferred metal ion as magnesium is known to have neuroprotective effects. The metal ion is in part chelated by a non-steroidal anti-inflammatory drug that does not inhibit platelet activity and includes salicylate and ibuprofenate. The complex also includes a ligand operative in transport across the blood brain barrier.

A process for making an inventive complex includes the stoichiometric addition of ligands containing carboxylate groups to a solution of the metal ion. In instances where the metal ion is magnesium(II), a stoichiometric ratio of 1:1:1 is found between the non-steroidal anti-inflammatory ligand: magnesium(II):transporter ligand.

DETAILED DESCRIPTION OF THE INVENTION

The present invention provides a method for treating neuronal injuries, diseases, conditions, disorders, pain including neurogenic pain, neuronal injury caused by inflammatory conditions, or neurotrauma often associated with traumatic brain injury (TBI) and/or spinal cord trauma (SCT), including diffuse axonal injuries manifested in conditions such as dystonia/spasticity, spastic disorders, convulsive disorders, or epilepsy by administering into a patient or subject having or suspected of having or developing diffuse axonal injuries a therapeutically effective amount of a non-steroidal anti-inflammatory drug conjugate compound capable of traversing the blood brain barrier.

The terms "patient" and "subject" mean all animals including humans. Examples of patients or subjects include humans, cows, dogs, cats, goats, sheep, and pigs.

Those skilled in the art are easily able to identify patients or subjects having diffuse axonal injuries including conditions such as dystonia/spasticity, spastic disorders, convulsive disorders, and epilepsy, for example, patients who have sustained traumatic brain injury induced dystonia/spasticity. Additionally, patients or subjects having pain or inflammatory conditions affecting the nervous system such as lupus and other inflammatory neuropathies, infections, acquired disorders such as multiple sclerosis, transverse myelitis, Parkinson's disease, CNS vasculitis, and Alzheimer's disease.

A therapeutically effective amount is an amount of the non-steroidal anti-inflammatory drug conjugate that when administered to a patient or subject, ameliorates a symptom of the condition or disorder.

Studies are demonstrating that there will be reduced injury at the site of neurologic lesion, particularly those areas that would be most proximal to the flow of CSF. These areas of the CNS include those injured during high speed motor vehicle crashes associated with diffuse axonal injury (DAI), which accounts for 50% of TBI, anoxic TBI (oxygen deprivation to the brain) and most cases of SCI.

The conjugate compounds of the present invention can be administered to a patient either alone or as part of a pharmaceutical composition. The compositions can be administered to patients either intrathecally or intraventricularly.

The conjugate compounds of the present invention can be administered to a patient either alone or as part of a pharmaceutical composition. The inventive compositions are suitable for administration to patients by a variety of routes including intrathecally, intraventricularly, intravenously, orally, parenterally, and mucosally.

Compositions suitable for administration may include physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents or vehicles include water, ethanol, polyols (propylene glycol, polyethylene glycol, glycerol, and the like), suitable mixtures thereof, vegetable oils (such as olive oil) and injectable organic esters such as ethyloleate. Proper fluidity can be maintained, for example, by the use of a coating such as lecithin, by the maintenance of the required particle size in the case of dispersions, and by the use of surfactants.

In a preferred embodiment, the non-steroidal anti-inflammatory drug includes magnesium salicylate conjugated to a transporter species delivered in concert with choline, or a substituted form of salicylate.

The term "substituted" means that the base organic radical has one or more substituents.

Compounds which do not inhibit platelets and which are still potent NSAIDs are salicylate and ibuprofen. Preferably, a metal ion complex of salicylate or ibuprofen is provided. More preferably the metal ion is magnesium. Since magnesium may have neuroprotective effects as well as blocking N-methyl-D-aspartase (NMDA) channels in a voltage dependent manner (Mayer et al. *Nature* 1984; 309:261–3; Nowak et al. *Nature* 1984; 307:462–5) thereby interrupting a well known pathway for cell death.

The inventive drug compounds are able to cross over to the CNS. The inventive compounds reduce the amount of neurological injury whether induced by trauma, ischemia, hemorrhage, tumors, or inflammatory conditions to the affected areas that are contiguous to delivery in the CSF. This would include inflammatory conditions such as cerebral vasculitis and cerebral sarcoid.

It has been clearly demonstrated that following head injury, traumatic brain injury, and spinal cord injury, that prostaglandin synthesis increases (Shohami et al. *J. Cerebral Blood Flow and Metabolism* 1987; 7:58–63). Therefore, other inflammatory factors should respond to NSAIDs if delivered quickly and to the right location. However, all of these prior studies have failed because the drugs used affected platelets thereby inactivating them or failed to cross the blood brain barrier.

An inventive conjugate has the formula

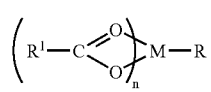

where $R^1$ is

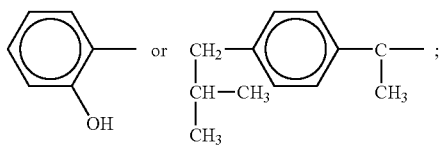

n is an integer 1 or 2; M is a metal cation Ca(II), Mg(II), Cu(II), Ni(II); R is a moiety capable of crossing the blood brain barrier and includes blood brain barrier (BBB) peptide, transferrin, TAT peptides, bradykinin, beta-endorphin, bombesin, calcitonin, cholecystokinin, an enkephalin, dynorphin, insulin, gastrin, substance P, neurotensin, glucagon, secretin, somatostatin, motilin, vasopressin, oxytocin, prolactin, thyrotropin, an angiotensin, galanin, neuropeptide Y, thyrotropin-releasing hormone, gonadotropnin-releasing hormone, growth hormone-releasing hormone, luteinizing hormone, vasoactive intestinal peptidemembrane transport protein, gluconate, L-lactate, L-leucine, L-tryptophan, and L-glutamate. An inventive conjugate being formed preferably through the chelation of a magnesium ion by the carboxyl groups of ibuprofenate or salicylate and the carboxyl groups of a transporter moiety. It is appreciated that salicylate and USP grade water soluble magnesium salts are inexpensive starting reagents for chelation to a transporter moiety R. The small size of magnesium salicylate precludes many of the transmembrane transport problems associated with larger molecules.

According to the present invention, a magnesium salicylate conjugate is formed to a species known to traverse the blood brain barrier either through diffusion or a specific transporter. Owing to the small molecular weight and lack of steric hindrance associated with magnesium salicylate, inhibitory effects on the transporter species associated with conjugation are limited.

An inventive conjugate includes a transporter moiety R having a privileged ability to pass the blood brain barrier and thereafter be cleaved from a magnesium salicylate component to itself form an active therapeutic or neurochemistry equilibrium modifier. The ability to deliver as a conjugate magnesium salicylate with a second neuroactive species provides a previously unavailable ability to moderate a neurological therapeutic effect. As neuroactive compounds are subject to complex feedback mechanisms, the successful transport of a compound across the blood brain barrier has a moderated therapeutic effect owing to neurochemistry equilibrium shifts in response to the compound traversing the barrier. An inventive conjugate provides magnesium salicylate that upon cleavage from the transporter moiety R is in proximity to a second neurologically active species that has an agonistic, antagonistic, or independently operating neuroactive species. The aminobutyramide and moiety R after cleavage being subject to further enzymatic modification. The simultaneous dosage of magnesium salicylate and the neuroactive transporter moiety R upon cleavage assures the desired dose is present. It is appreciated that two or more inventive conjugates are amenable to simultaneous delivery in order to provide still more refined therapeutic affects.

An inventive conjugate is preferably formed through a coordinate linkage between a magnesium ion, a salicylate and a carboxylate containing blood brain barrier transporter compound. A carboxylated blood brain barrier transporter compounds operative herein illustratively includes amino acids and polypeptides such as leucine, tryptophan, BBB, TAT, bradykinin, beta-endorphin, bombesin, calcitonin, cholecystokinin, an enkephalin, dynorphin, insulin, gastrin, substance P, neurotensin, glucagon, secretin, somatostatin, motilin, vasopressin, oxytocin, prolactin, thyrotropin, an angiotensin, galanin, neuropeptide Y, thyrotropin-releasing hormone, gonadotropnin-releasing hormone, growth hormone-releasing hormone, luteinizing hormone, vasoactive intestinal peptide and transferrin.

Optionally, a linker species is provided intermediate between the transporter moiety R and the metal ion —$R^1$ portion of an inventive conjugate. The linker in simplest form includes a carboxyl moiety and a moiety reactive with the transporter compound. Substituents extending from a linker are provided to modify the lipophilicity of an inventive conjugate, or tether a dye or spectroscopic marker. With the inclusion of a linker, care should be taken to limit both the molecular weight and the hydrophilicity of the linker in order to retain the ability to traverse the blood brain barrier. Transporter compound reactive moiety of the linker is dependent upon the transporter compound moiety to be bound thereto. Suitable chemistries for a variety of potential reaction moieties are found in *Comprehensive Organic Transformations*, R. C. Larock, John Wiley & Sons 1999.

It is appreciated that a linker, when present, is the preferred site for the attachment of an additional species. A substituent is optionally provided pendent from the linker backbone. The substituent illustratively includes a radioactive atom, a magnetic spectroscopically active marker and an organic dye. A radioactive atom is alternatively operative as a marker in isotope studies such as positron emission tomography, single photon emission computer tomography, radiological studies and the like. Common radio-isotopes used in medical imaging illustratively include $^{123}$I, $^{99m}$Tc, and other chelated radioisotopes as detailed in U.S. Pat. No. 6,241,963. Spectroscopically active markers include NMR/MRI active contrast enhancing moieties known to the art such as gadolinium, as detailed in "Contrast Agents 1: Magnetic Resonance Imaging" (Topics in Current Chemistry, 221) by Werner Krause, Springer Verlag, Berlin, Germany. Organic dyes, while recognized to have potentially distinct NMR/MRI signatures, are provided to yield an optically active spectroscopic signature suitable for biopsy, surgical identification, or preclinical studies of tissue treated by an inventive compound.

Compositions suitable for injection optionally include physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

An inventive conjugate is formed by dissolving a metal ion containing salt in a suitable solvent. Metal ions operative herein illustratively include calcium, magnesium, copper (II), and nickel(II). Drug complex conjugates are typically formed by dissolving a metal ion containing salt in a suitable solvent such as water, ethanol, isopropanol, or tetrahydrofuran. To the metal ion solution a stoichiometric molar quantity of salicylate or ibuprofen $R^1$ is added along with a stoichiometric amount of the transporter R. The resulting solution is reduced in volume by evaporation and left to crystallize. The inventive complex conjugate is filtered and purified to pharmaceutical purity.

Inventive compositions optionally contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example, sugars, sodium chloride, and the like. Prolonged absorption of the injectable pharmaceutical form can be brought about by the use of agents delaying absorption, for example, aluminum monostearate and gelatin.

The complex conjugates of the present invention can be administered to a patient at dosage levels in the range of about 100 mg to about 1500 mg per day of salicylate or ibuprofen. The specific dosage used, however, can vary. For example, the dosage can depend on a number of factors including the requirements of the patient, the severity of the condition being treated, and the pharmacological activity of the compound being used. The determination of optimum dosages for a particular patient is well known to those skilled in the art.

As stated above, intrathecal, intravenous, intramuscular, and intraventricular administration of inventive complex conjugates is operative. Examples of well-known implants and modules useful in the present invention for intrathecal or intraventricular administration include: U.S. Pat. No. 4,487,603, which discloses an implantable micro-infusion pump for dispensing medication at a controlled rate; U.S. Pat. No. 4,486,194, which discloses a therapeutic device for administering medicaments through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are well known to those skilled in the art.

Compositions suitable for injection optionally include physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example, sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others well known in the art. They may contain opacifying agents, and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients.

The enteric coating is typically a polymeric material. Preferred enteric coating materials have the characteristics of being bioerodible, gradually hydrolyzable and/or gradually water-soluble polymers. The amount of coating material applied to a solid dosage generally dictates the time interval between ingestion and drug release. A coating is applied with to a thickness such that the entire coating does not dissolve in the gastrointestinal fluids at pH below 5 associated with stomach acids, yet dissolves above pH 5 in the small intestine environment. It is expected that any anionic polymer exhibiting a pH-dependent solubility profile is readily used as an enteric coating in the practice of the present invention to achieve delivery of the active to the lower gastrointestinal tract. The selection of the specific enteric coating material depends on properties such as resistance to disintegration in the stomach; impermeability to gastric fluids and active agent diffusion while in the stomach; ability to dissapate at the target intestine site; physical and chemical stability during storage; non-toxicity; and ease of application.

Suitable enteric coating materials illustratively include-cellulosic polymers such as hydroxypropyl cellulose, hydroxyethyl cellulose, hydroxypropyl methyl cellulose, methyl cellulose, ethyl cellulose, cellulose acetate, cellulose acetate phthalate, cellulose acetate trimellitate, hydroxypropylmethyl cellulose phthalate, hydroxypropyhnethyl cellulose succinate and carboxymethylcellulose sodium; acrylic acid polymers and copolymers, preferably formed from acrylic acid, methacrylic acid, methyl acrylate, ammonio methylacrylate, ethyl acrylate, methyl methacrylate and/or ethyl; vinyl polymers and copolymers such as polyvinyl pyrrolidone, polyvinyl acetate, polyvinylacetate phthalate, vinylacetate crotonic acid copolymer, and ethylene-vinyl acetate copolymers; shellac; and combinations thereof. A particularly preferred enteric coating material for use herein are those acrylic acid polymers and copolymers available under the tradename EUDRAGIT®, Roehm Pharma (Germany). The EUDRAGIT® series L, L-30D and S copolymers are most preferred since these are insoluble in stomach and dissolve in the intestine.

The enteric coating provides for controlled release of the active agent, such that release is accomplished at a predictable location in the lower intestinal tract below the point at which drug release would occur absent the enteric coating. The enteric coating also prevents exposure of the active agent and carrier to the epithelial and mucosal tissue of the buccal cavity, pharynx, esophagus, and stomach, and to the enzymes associated with these tissues. The enteric coating therefore helps to protect the active agent and a patient's internal tissue from any adverse event prior to drug release at the desired site of delivery. Furthermore, the coated solid dosages of the present invention allow optimization of drug absorption, active agent protection, and safety. Multiple enteric coatings targeted to release the active agent at various regions in the lower gastrointestinal tract would enable even more effective and sustained improved delivery throughout the lower gastrointestinal tract.

The enteric coating optionally contains a plasticizer to prevent the formation of pores and cracks that allow the penetration of the gastric fluids into the solid dosage. Suitable plasticizers illustratively include, triethyl citrate (Citroflex 2), triacetin (glyceryl triacetate), acetyl triethyl citrate (Citroflec A2), Carbowax 400 (polyethylene glycol 400), diethyl phthalate, tributyl citrate, acetylated monoglycerides, glycerol, fatty acid esters, propylene glycol, and dibutyl phthalate. In particular, a coating composed of an anionic carboxylic acrylic polymer typically contains approximately 10% to 25% by weight of a plasticizer, particularly dibutyl phthalate, polyethylene glycol, triethyl citrate and triacetin. The coating can also contain other coating excipients such as detackifiers, antifoaming agents, lubricants (e.g., magnesium stearate), and stabilizers (e.g., hydroxypropylcellulose, acids and bases) to solubilize or disperse the coating material, and to improve coating performance and the coated product.

The enteric coating is applied to a solid dosage using conventional coating methods and equipment. For example, an enteric coating can be applied to a solid dosage using a coating pan, an airless spray technique, fluidized bed coating equipment, or the like. Detailed information concerning materials, equipment and processes for preparing coated dosage forms may be found in Pharmaceutical Dosage Forms: Tablets, eds. Lieberman et al. (New York: Marcel Dekker, Inc., 1989), and in Ansel et al., Pharmaceutical Dosage Forms and Drug Delivery Systems, 6.sup.th Ed. (Media, Pa.: Williams & Wilkins, 1995).

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

Besides such inert diluents, the composition can also include adjuvants, such as wetting agents, emulsifying and suspending agents, sweetening, flavoring, and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

An inventive compound is also delivered in conjunction with an active therapeutic compound. The therapeutic compound illustratively being active as antibiotic, a gamma or beta radiation emitting species, an anti-inflammatory, an antitumoral, an antiviral, an antibody, a hormone, an enzyme, and antigenic peptide or protein.

The following examples are presented below to illustrate particular embodiments of the invention and are not intended to limit the scope of the specification, including the claims, in any way.

EXAMPLE 1

Synthesis of Salicylate Magnesium(II) Membrane Translocating Peptide Conjugate

Magnesium hydroxide (0.0116 g; 0.0002 mol) is dissolved in 100 ml of water by gradual stirring. 0.03 g (0.0002 mols) of sodium salicylate is added to the solution to yield a magnesium salicylate molar ratio of 1:1. The resulting solution added to a 300 ml solution containing 0.225 g of membrane translocating peptide. The resulting solution is stirred at 4° Celsius for 12 hours and lyophilized to a volume of 200 ml. The solution is left to precipitate an inventive complex. The complex is filtered, washed with ether and purified commensurate with pharmaceutical purity requirements.

EXAMPLE 2

Ibuprofen Magnesium Gluconate

Magnesium hydroxide (1.16 g; 0.02 mol) is dissolved in 100 ml of water by gradual stirring. To the solution 0.02 mol of the sodium salt of ibuprofen is added with gradual stirring followed by 0.02 mol of sodium gluconate to form a molar stoichiometric ratio of ibuprofen:magnesium(II):gluconate of 1:1:1. The solution is reduced to half volume at room temperature and left to crystallize. An inventive complex is filtered from the solution, washed with ether and dried at room temperature. The hexadentate magnesium complex that results is identified as magnesium ibuprofate gluconate dihydrate.

EXAMPLE 3

Intravenous Magnesium(II) Gluconate Salicylate for Pain

Magnesium(II) gluconate salicylate is formed according to Example 2 with the replacement of ibuprofen by salicylate. Two rats with chronic spinal cord injury are chosen because they consistently exhibited allodynia. A 1-French silicon tubing catheter is threaded into the femoral vein. The femoral catheter is connected an ESOX that is implanted subcutaneously. The ESOX pump flowed at a rate of 60 µl per day. Initially, saline is placed in the pumps. At testing on days 2, 12, 14 after pump placement, signs of allodynia are consistently observed when the animals are lightly touched at particular parts of their body (left flank for rat 1 and right shoulder for rat 2). Animals vocalized consistently when these areas are lightly touched. All of the behavioral testing is done by a person who was unaware of the type of drug delivered or the expected effects of the drug. The saline is removed from the pumps and the pumps were refilled with Mg(II) gluconate salicylate. On repeated tested of these animals, no evidence of allodynia is observed. When the salicylate is removed and replaced with saline, consistent allodynia is observed.

EXAMPLE 4

Intravenous Mg(II) Gluconate Ibuprofenate for Treatment of Acute Pain

Male Sprague-Dawley rats are deeply anesthetized with a mixture of halothane and oxygen and a femoral catheter is inserted using sterile technique. The distal end of the catheter accessible for bolus injections. Group 1 (acute pain, cutaneous and visceral) rats are allowed to recover overnight and Group 2 (persistent pain, formalin test) rats allowed to recover for one week prior to further testing.

Rats are assigned to one of four subgroups (n=5–6/subgroup). On the day of testing these rats are lightly anesthetized with inhaled halothane (0.5–0.8%) in oxygen delivered by facemask and baseline responses obtained for the tail flick test and the colorectal distension test. Each subgroup then subsequently received a 20 ml bolus dose of Mg(II) gluconate salicylate (0, 2.5, 5 or 10 mg using a 500 mg/ml solution) and/or normal saline. These rats are then tested using both the tail flick and colorectal distension tests at four minute intervals beginning one minute after the bolus dose.

The tail of the lightly anesthetized rat is placed on the testing apparatus and a 1.5×11 mm area of the ventral surface of the middle third of their tail exposed to radiant heat (projector bulb). The tail flick latency is defined as the latency from the onset of tail heating movement to the flexion-withdrawal reflex movement of the tail as determined using a photoelectric device and measured to the nearest 0.1 second. The tail is removed from heat if there was no movement within eight seconds to avoid damage to the tail.

Mg(II) gluconate salicylate produced a dose dependent response. In those tests the response to the bolus is rapid in onset.

EXAMPLE 5

Subcutaneous Mg(II) Salicylate Transporter Peptide to Prevent Secondary Damage and Inflammation Following Spinal Cord Injury In this study, twenty-four deeply anesthetized rats received a moderate to severe spinal cord injury using a 2-French Fogarty embolectomy catheter. After injury, each rat was given daily injection subcutaneously with a 25 gauge needle of 60 µl of either saline or the Mg complex in saline solution. Animals are randomly assigned to receive saline or magnesium complex. Animals are tested each week using the BBB locomotor test. All of the behavioral testing is done by a person who was unaware of the type of drug delivered or the expected effects of the drug. Animals that received the magnesium complex exhibited on average less functional deficits.

In view of the teaching presented herein, other modifications and variations of the present invention will readily be apparent to those of skill in the art. The discussion and description are illustrative of some embodiments of the present invention, but are not meant to be limitations on the practice thereof. It is the following claims, including all equivalents, which define the scope of the invention.

Any patents, applications, or publications mentioned in the specification are indicative of the levels of those skilled in the art to which the invention pertains. These patents, applications, and publications are herein incorporated by reference to the same extent as if each individual publication was specifically and individually indicated to be incorporated by reference.

The invention claimed is:

1. A complex having the formula:

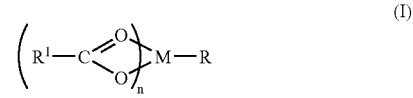

where $R^1$ is

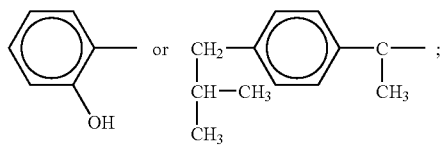

M is a metal ion Ca(II), Mg(II), Cu(II) or Ni(II); n is an integer 1 or 2; R is BBB peptide, transferrin, membrane transporter peptide, TAT peptide, bradykinin, beta-endorphin, bombesin, calcitonin, cholecystokinin, an enkephalin, dynorphin, insulin, gastrin, substance P, neurotensin, glucagon, secretin, somatostatin, motilin, vasopressin, oxytocin, prolactin, thyrotropin, an angiotensin, galanin, neuropeptide Y, thyrotropin-releasing hormone, gonadotropnin-releasing hormone, growth hormone-releasing hormone, luteinizing hormone, vasoactive intestinal peptidegluconate, L-lactate, L-leucine, L-tryptophan, and L-glutamate; and R is coupled to M through a carboxylate moiety.

2. The complex of claim 1 wherein M is magnesium(II).
3. The complex of claim 2 wherein n is two.
4. The complex of claim 1 wherein R is gluconate.
5. The complex of claim 4 wherein $R^1$ is

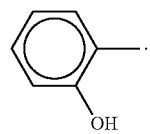

6. The complex of claim 4 wherein $R^1$ is

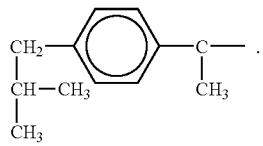

7. The complex of claim 1 wherein R is an amino acid selected from the group consisting of L-glutamate, L-leucine, and L-tryptophan.

8. The complex of claim 1 further comprising a linker L interposed between R and the remainder of the complex.

9. The complex of claim 8 wherein said linker has an alkyl backbone of less than eight carbon atoms.

10. The complex of claim 8 wherein said backbone is linked to M through a carboxylate.

11. The compound of claim 8 wherein said linker has a pendent substituent, the pendent substituent comprising at least one moiety selected from the group consisting of: a radioactive atom, a spectroscopically active marker, and an organic dye.

12. The compound of claim 8 wherein said linker is a terminal amino carboxylic acid.

13. A therapeutic composition comprising the compound of claim 1 in a physiologically suitable solvent for administration by a route selected from the group consisting of: parenteral, intraventricular, and intrathecal.

14. The composition of claim 13 further comprising an adjuvant.

15. A process for forming a metal ion complex capable of crossing the blood brain barrier having the formula

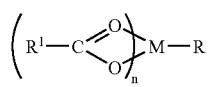 (I)

comprising chelating the metal ion M where M is Ca(II), Mg(II), Cu(II) or Ni(II) with $R^1$ where $R^1$ is

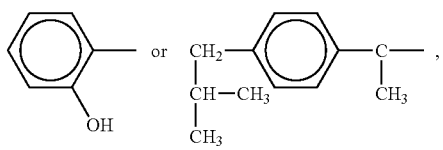, chelating the metal ion M with R where R is BBB peptide, transferrin, membrane transporter peptide, TAT peptide, bradykinin, beta-endorphin, bombesin, calcitonin, cholecystokinin, an enkephalin, dynorphin, insulin, gastrin, substance P, neurotensin, glucagon, secretin, somatostatin, motilin, vasopressin, oxytocin, prolactin, thyrotropin, an angiotensin, galanin, neuropeptide Y, thyrotropin-releasing hormone, gonadotropnin-releasing hormone, growth hormone-releasing hormone, luteinizing hormone, vasoactive intestinal peptidegluconate, L-lactate, L-leucine, L-tryptophan, and L-glutamate; and R is coupled to M through a carboxylate moiety; and isolating a complex of Formula (I).

16. The process of claim 15 wherein M is magnesium(II) and R, Mg, and

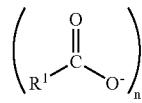

are present in the complex in a stoichiometric ratio of 1:1:1.

17. The process of claim 16 wherein n is two.
18. The process of claim 16 wherein R is gluconate.
19. The process of claim 16 wherein $R^1$ is

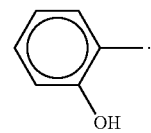

20. The process of claim 16 wherein $R^1$ is

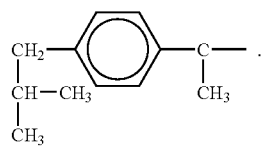

21. The process of claim 16 wherein R is an amino acid selected from the group consisting of L-glutamate, L-leucine, and L-tryptophan.

22. The process of claim 15 wherein chelation of M with R occurs prior to chelation of M with

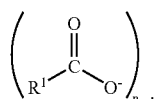 .

23. The process of claim 15 wherein chelation of M occurs simultaneously with both R and

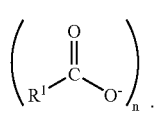 .

24. The process of claim 15 wherein chelation of M with either R or

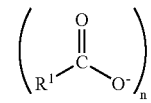

occurs in the presence of water.

* * * * *